(12) United States Patent
Conley et al.

(10) Patent No.: US 10,561,176 B2
(45) Date of Patent: Feb. 18, 2020

(54) VAPING ATOMIZER

(71) Applicant: FUMA INTERNATIONAL LLC, Medina, OH (US)

(72) Inventors: Gregory D. Conley, Medina, OH (US); Daniel C. Hillenbrandt, Jr., Medina, OH (US); Rebecca L. Conley, Medina, OH (US)

(73) Assignee: FUMA INTERNATIONAL, LLC, Medina, OH (US)

( * ) Notice: Subject to any disclaimer, the term of this patent is extended or adjusted under 35 U.S.C. 154(b) by 0 days.

(21) Appl. No.: 16/164,245

(22) Filed: Oct. 18, 2018

(65) Prior Publication Data
US 2019/0116884 A1 Apr. 25, 2019

Related U.S. Application Data

(60) Provisional application No. 62/707,072, filed on Oct. 19, 2017.

(51) Int. Cl.
| | |
|---|---|
| *A24F 13/00* | (2006.01) |
| *A24F 47/00* | (2020.01) |
| *H05B 3/44* | (2006.01) |
| *A61M 15/06* | (2006.01) |
| *H05B 1/02* | (2006.01) |

(Continued)

(52) U.S. Cl.
CPC ......... *A24F 47/008* (2013.01); *A61M 11/042* (2014.02); *A61M 15/06* (2013.01); *H05B 1/0227* (2013.01); *H05B 3/44* (2013.01); *A61M 15/002* (2014.02); *A61M 2205/8206* (2013.01)

(58) Field of Classification Search
CPC ...................................................... A24F 47/00
USPC ................................................. 131/328–329
See application file for complete search history.

(56) References Cited

U.S. PATENT DOCUMENTS

| | | |
|---|---|---|
| 9,629,394 B2 | 4/2017 | Aronie et al. |
| D800,382 S | 10/2017 | Mathias et al. |
| 9,795,168 B2 | 10/2017 | Zhu |

(Continued)

OTHER PUBLICATIONS

Internet advertisement for Joyetech ProCore Aries Tank dated at least as early as Oct. 3, 2017.

(Continued)

*Primary Examiner* — Phuong K Dinh (74) *Attorney, Agent, or Firm* — Martin & Ferraro, LLP (57) ABSTRACT

A vaping atomizer for use with a vaping device is provided. The atomizer includes an enclosure portion and a heating-element housing extending through the interior of the enclosure portion. A first cavity for receiving vaping liquid is at least partially formed between the enclosure portion and the heating-element housing. The heating-element housing includes at least one aperture formed therein facilitating transfer of the vaping liquid from the first cavity to a second cavity formed on the interior thereof. The at least one aperture formed in the heating-element housing can be generally shaped as a triangle. The size and shape of the least one aperture can be optimized to prevent the vaping liquid from flooding the interior cavity, and to accommodate uses of various vaping liquids having different viscosities, as well as to prevent liquid-absorbing material provided in the second cavity from drying out to prevent dry hits during use of the vaping atomizer.

20 Claims, 8 Drawing Sheets

(51) Int. Cl.
*A61M 11/04* (2006.01)
*A61M 15/00* (2006.01)

(56) References Cited

U.S. PATENT DOCUMENTS

| | | | |
|---|---|---|---|
| 9,795,169 B1 | 10/2017 | Zhu | |
| 9,795,170 B1 | 10/2017 | Zhu | |
| 9,814,264 B2 | 11/2017 | Coelho Belo Fernandes De Carvalho | |
| D804,718 S | 12/2017 | Mathias et al. | |
| 9,854,848 B1 | 1/2018 | Servutas | |
| 9,861,134 B2 | 1/2018 | Zhu | |
| 9,883,698 B2 | 2/2018 | Zhu | |
| 9,883,699 B2 | 2/2018 | Zhu | |
| 9,907,341 B1 | 3/2018 | Zhu | |
| 9,913,496 B2 | 3/2018 | Lin | |
| 9,918,496 B2 | 3/2018 | Kane et al. | |
| 9,924,744 B2 | 3/2018 | Lin | |
| 9,980,517 B2 | 5/2018 | Zhu | |
| 10,021,911 B2 | 7/2018 | Xu | |
| 10,080,387 B2 | 9/2018 | Phillips et al. | |
| 10,085,485 B2 | 10/2018 | Hunt et al. | |
| 10,111,469 B2 | 10/2018 | Zhu | |
| 10,123,568 B1 | 11/2018 | Zhu | |
| 10,182,599 B2 | 1/2019 | Zhu | |
| 10,201,189 B1 | 2/2019 | Qiu | |
| 10,306,928 B2 | 6/2019 | Qiu | |
| 10,306,930 B2 | 6/2019 | Qiu | |
| 10,334,877 B2 | 7/2019 | Qiu | |
| 10,433,588 B2 | 10/2019 | Coelho Belo Fernandes De Carvalho | |
| 2016/0183596 A1* | 6/2016 | Rado | A24F 47/008 392/395 |
| 2016/0249681 A1* | 9/2016 | Liu | A24F 47/008 392/404 |
| 2017/0013880 A1* | 1/2017 | O'Brien | A24F 47/008 |
| 2017/0295845 A1* | 10/2017 | Bajpai | A24F 47/008 |

OTHER PUBLICATIONS

Screenshot of archived page of Joyetech.com dated Dec. 3, 2016 from Archive.org (waybackmachine).
Screenshot of archived page of Joyetech.com dated Apr. 19, 2017 from Archive.org (waybackmachine).

* cited by examiner

VAPING ATOMIZER

The present application claims benefit of U.S. Provisional Application No. 62/707,072, filed Oct. 19, 2017; all of which is incorporated by reference herein.

FIELD

The present technology is generally related to a vaping atomizer employing a heating-element housing having various apertures affording passage of a vaping liquid therethrough into a liquid absorbing material provided in the heating-element housing.

BACKGROUND

Vaping devices can employ atomizers to facilitate vaping of vaping liquids. Typically, the atomizers include an interior cavity for holding a vaping liquid. The atomizers also typically include a heating-element housing into which the vaping liquid is transferred for vaporization. The heating-element housing includes a liquid-absorbing material and a heating element provided on the interior thereof. The liquid-absorbing material absorbs the vaping liquid and the heating element heats the interior of the heating-element housing to vaporize the liquid contained in the liquid-absorbing material. The vaping liquid is transferred from the interior cavity for holding the vaping liquid into the interior of the heating-element housing via apertures formed in the heating-element housing. However, there is a need to optimize the sizes and shapes of these apertures to prevent the vaping liquid from flooding the interior cavity, and to accommodate uses of various vaping liquids having different viscosities. Furthermore, there is a need to optimize the sizes and shapes of these apertures to prevent the liquid-absorbing material from drying out to prevent dry hits.

SUMMARY

The techniques of this disclosure generally relate to a vaping atomizer.

In one aspect, the present disclosure provides an atomizer for use with a vaping device, the atomizer including a first end, an opposite second end, and a mid-longitudinal axis extending through the first and second ends; a base portion being provided at or adjacent the first end; an enclosure portion supported by the base portion and extending from the base portion toward the second end, the enclosure portion including an interior; a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion; a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture having a maximum dimension aligned with the mid-longitudinal axis, and a plane perpendicular to the mid-longitudinal axis extends through a midpoint of the maximum dimension aligned with the mid-longitudinal axis, a first area of the at least one aperture above the plane being less than a second area of the at least one aperture below the plane; and a heating element disposed in the second cavity of the heating-element housing, the heating element being at least partially surrounded by the liquid-absorbing material; where the first cavity is adapted to receive a vaping liquid so that the vaping liquid can pass from the first cavity to the second cavity through the at least one aperture, the liquid-absorbing material being configured to absorb the vaping liquid when passing through the at least one aperture; and where heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

In another aspect, the disclosure provides an atomizer for use with a vaping device, the atomizer including a first end, an opposite second end, and a mid-longitudinal axis extending through the first and second ends; a base portion being provided at or adjacent the first end; an enclosure portion supported by the base portion and extending from the base portion toward the second end, the enclosure portion including an interior; a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion; a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture having a first maximum dimension aligned with the mid-longitudinal axis, a second maximum dimension perpendicular to the first maximum dimension, a first minimum dimension perpendicular to the first maximum dimension, and a plane perpendicular to the mid-longitudinal axis extends through a midpoint of the first maximum dimension aligned with the mid-longitudinal axis, a first area of the at least one aperture above the plane being less than a second area of the at least one aperture below the plane, the first minimum dimension being disposed in the first area, and the second maximum dimension being disposed in the second area; a heating element disposed in the second cavity of the heating-element housing, the heating element being at least partially surrounded by the liquid-absorbing material; where the first cavity is adapted to receive a vaping liquid so that the vaping liquid can pass from the first cavity to the second cavity through the at least one aperture, the liquid-absorbing material being configured to absorb the vaping liquid when passing through the at least one aperture; and where heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

In yet another aspect, the disclosure provides an atomizer for use with a vaping device, the atomizer including a first end, an opposite second end, and a mid-longitudinal axis extending through the first and second ends; a base portion being provided at or adjacent the first end; an enclosure portion supported by the base portion and extending from the base portion toward the second end, the enclosure portion including an interior; a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion; a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture being generally shaped as a triangle, the at least one aperture having a maximum dimension aligned with the mid-longitudinal axis, and a plane perpendicular to the mid-longitudinal axis extends through a midpoint of the maximum dimension aligned with the mid-longitudinal axis, a first area of the at least one aperture above the plane being less than a second area of the at least one aperture below the plane; and a heating element disposed in the second cavity of the heating-element housing, the heating element being at least partially surrounded by the liquid-absorbing material; where the first cavity is adapted to receive a vaping liquid so that the vaping liquid can pass from the first cavity to the second cavity through the at least one aperture, the liquid-absorbing material being configured to absorb the vaping liquid when passing through the at least one aperture; and where heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION OF THE PREFERRED EMBODIMENT

Figure 1:
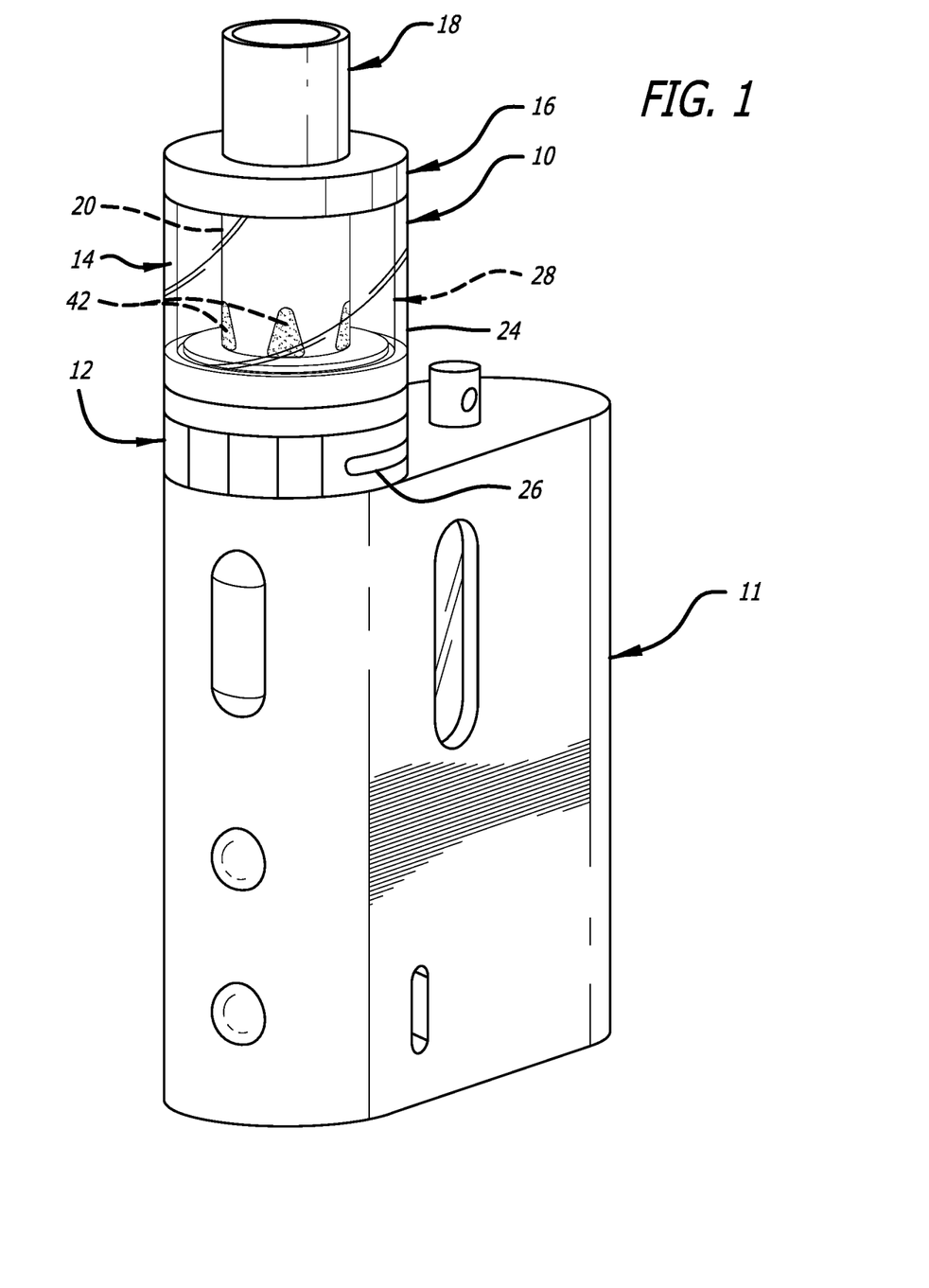
FIG. 1 is a perspective view illustrative of a vaping atomizer embodiment attached to a portable power source.
Figure 2:
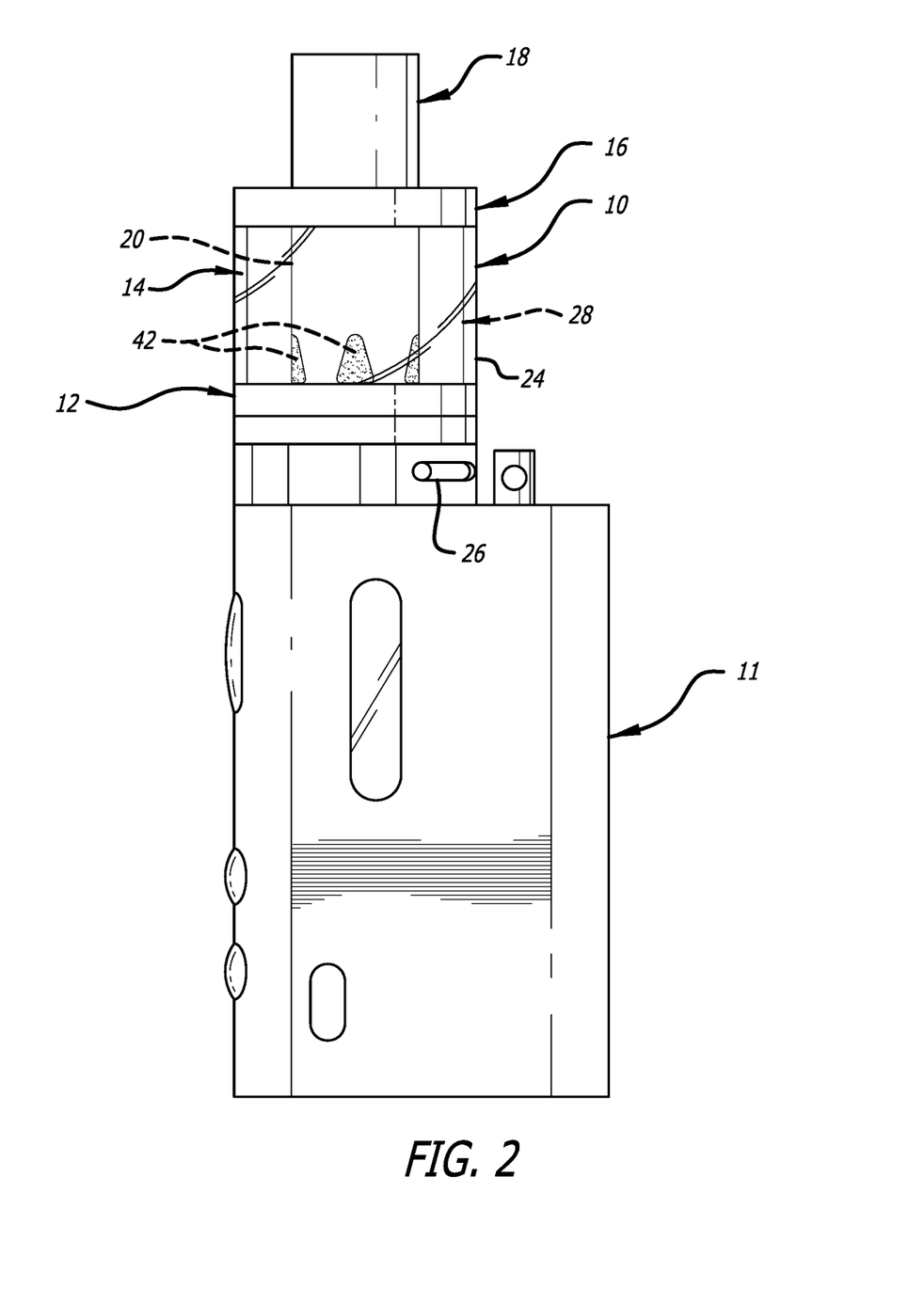
FIG. 2 is an elevational view illustrative of the vaping atomizer embodiment and portable power source of FIG. 1.
Figure 3:
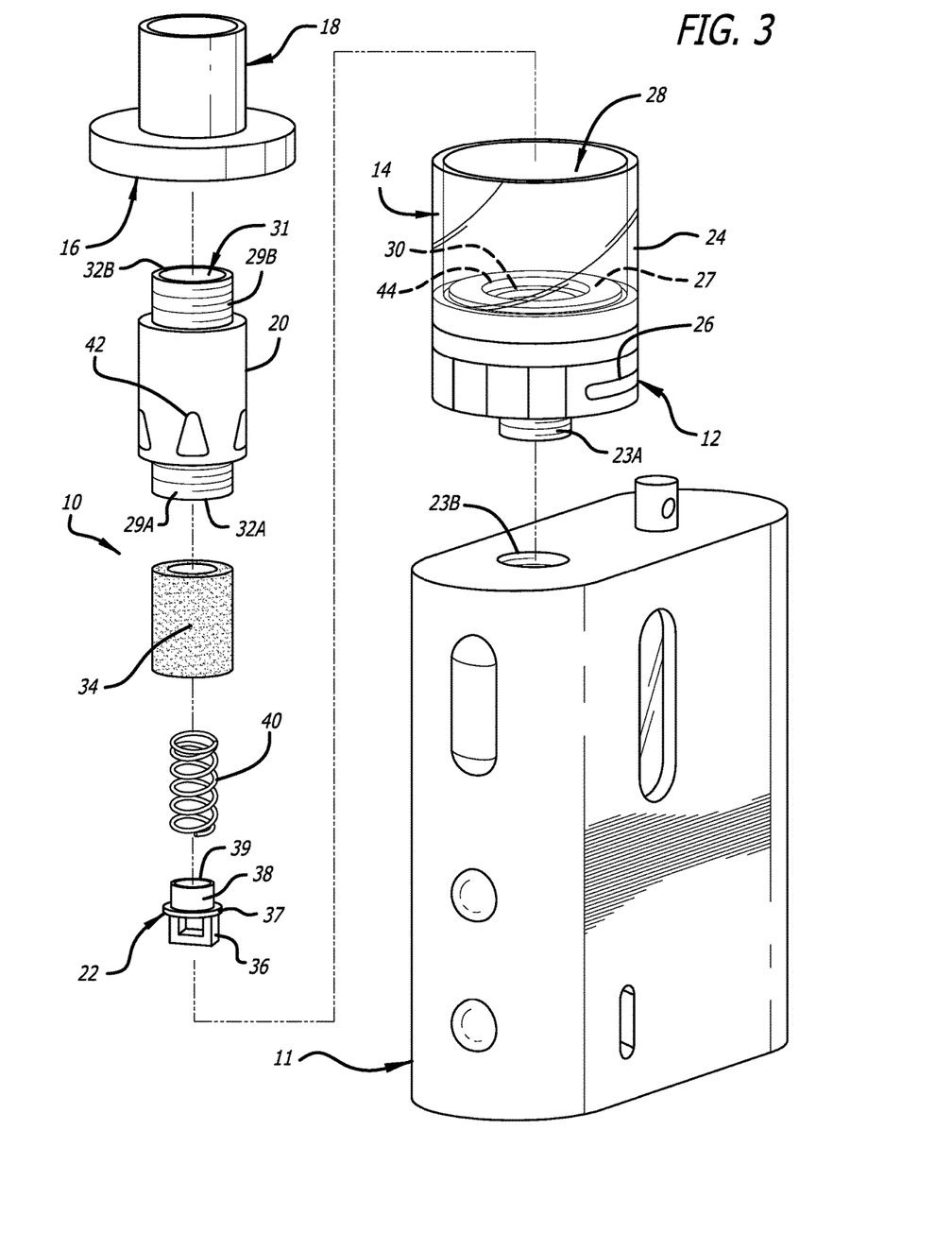
FIG. 3 is an exploded view illustrative of the vaping atomizer embodiment and the portable power source of FIG. 1.

A vaping atomizer according to a preferred embodiment of the present disclosure is generally referenced by the numeral 10 in FIGS. 1-7, 9, and 10. As discussed below, the atomizer 10, as depicted in FIGS. 1-3, can be configured for attachment to a portable power source 11 to supply electrical power used to facilitate heating of vaping liquid by the atomizer 10. As such, a user can use the atomizer 10 to vape the vaping liquid provided in the atomizer 10. The vaping liquid can include various liquid solutions that can be vaporized. The various liquid solutions can comprise tetrahydrocannabinol and cannabidiol, and the liquid solutions can be used for medicinal applications.

As depicted in FIGS. 1-4, the atomizer 10 can include a base portion 12, an enclosure portion 14, and a cap portion 16. The cap portion 16, as depicted in FIGS. 1-5, includes an inhaler portion 18. Furthermore, the enclosure portion 14, as depicted in FIGS. 1-4, 6, and 7, includes a heating-element housing 20 positioned therein, and the enclosure portion 14 is configured to receive and store an amount of the vaping liquid (not shown).

The base portion 12 of the atomizer 10 supports the enclosure portion 14 and the heating-element housing 20, and the base portion 12 includes at least one conductive element (not shown) to transmit electrical power from the power source 11 to a heating element 22 (FIGS. 3 and 5-7) provided within the heating-element housing 20. The base portion 12 and the power source 11 can include complimentary connectors 23A and 23B, respectively, facilitating attachment therebetween. Furthermore, in addition to the at least one conductive element, the base portion 12 also includes air passages (not shown) communicating with openings 26 (FIGS. 1-4, 9 and 10) formed therein. The air passages facilitate the passage of air from the openings 26 to the interior of the heating-element housing 20. The sizes of the openings 26 can be changed via manipulation between a fully open position (FIG. 9) and a fully closed position (FIG.

Figure 9:
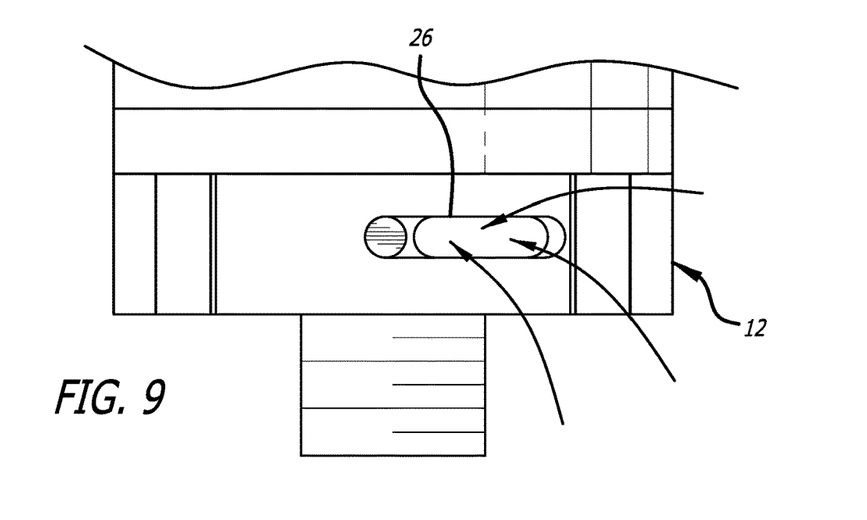
FIG. 9 is an enlarged partial elevational view illustrative of a bottom portion of the vaping atomizer of FIG. 1 depicting an opening(s) in a base portion of the vaping atomizer embodiment of FIG. 1 in the opened position.
Figure 10:
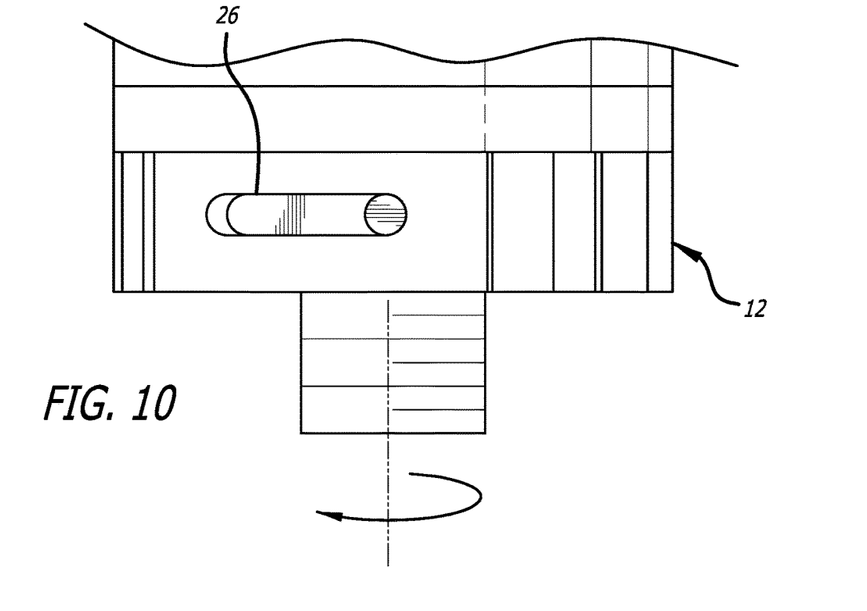
FIG. 10 is an enlarged partial elevational view illustrative of a bottom portion of the vaping atomizer of FIG. 1 depicting the opening(s) in the base portion of the vaping atomizer embodiment of FIG. 1 in the closed position.

10). The sizes of the openings 26 determines how much air can be drawn through the atomizer 10.

The enclosure portion 14, as depicted in FIGS. 1-4, 6, and 7, can be formed from a wall portion 24 that can be transparent. The wall portion 24 can be attached to the base portion 12 to provide a liquid-tight connection therebetween, and the wall portion 24 (along with an upper surface 27 of the base portion 12) defines an interior cavity 28 of the enclosure portion 14 for receiving a supply of the vaping liquid.

Figure 4:
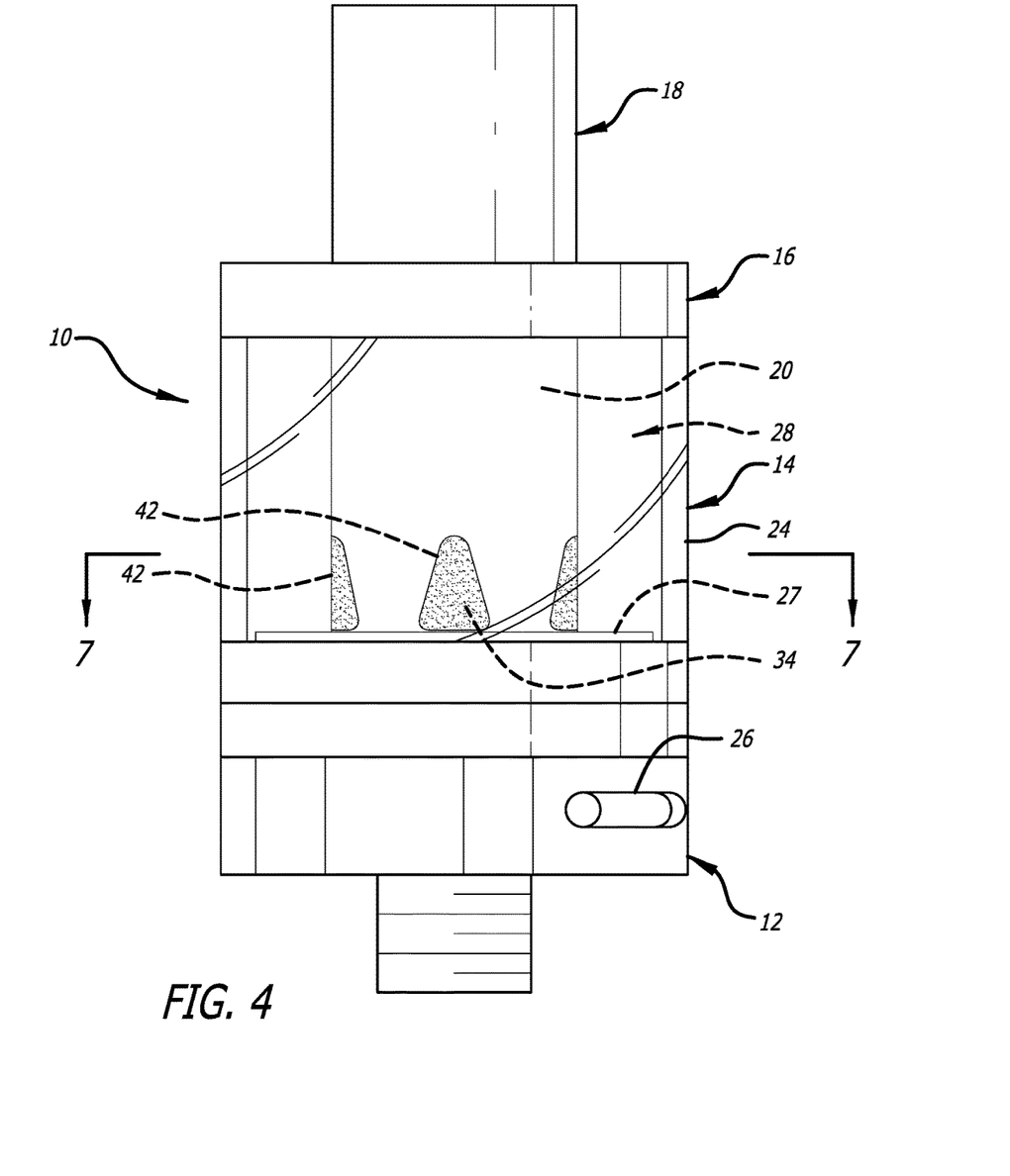
FIG. 4 is an elevational view illustrative of the vaping atomizer embodiment of FIG. 1.
Figure 5:
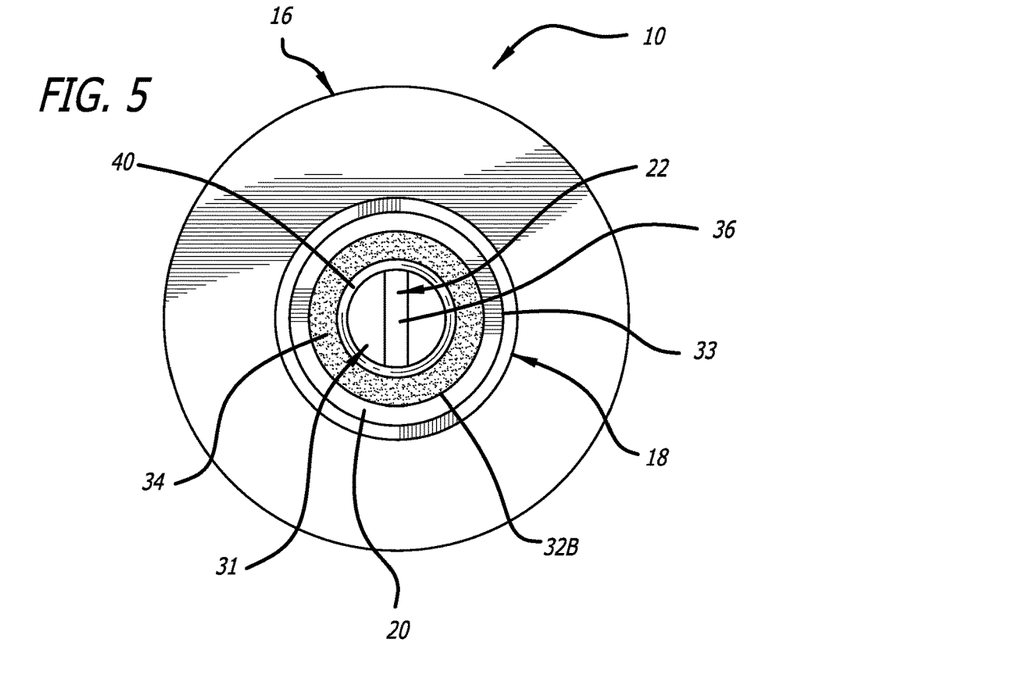
FIG. 5 is a top plan view illustrative of the vaping atomizer embodiment of FIG. 1 with a cap attached thereto.
Figure 6:
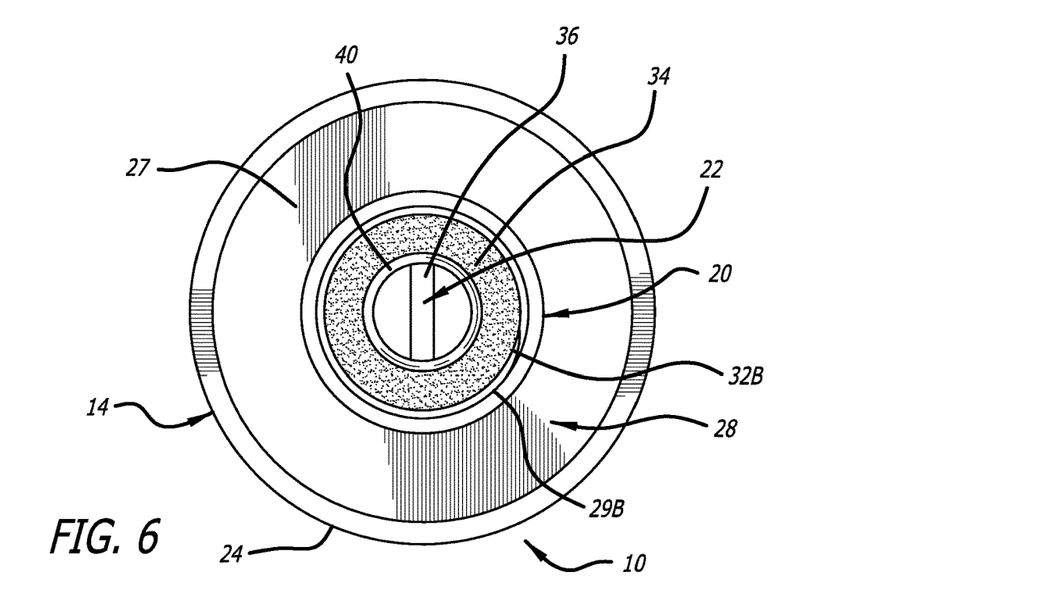
FIG. 6 is a top plan view illustrative of the vaping atomizer embodiment of FIG. 1 with the cap detached therefrom.
Figure 7:
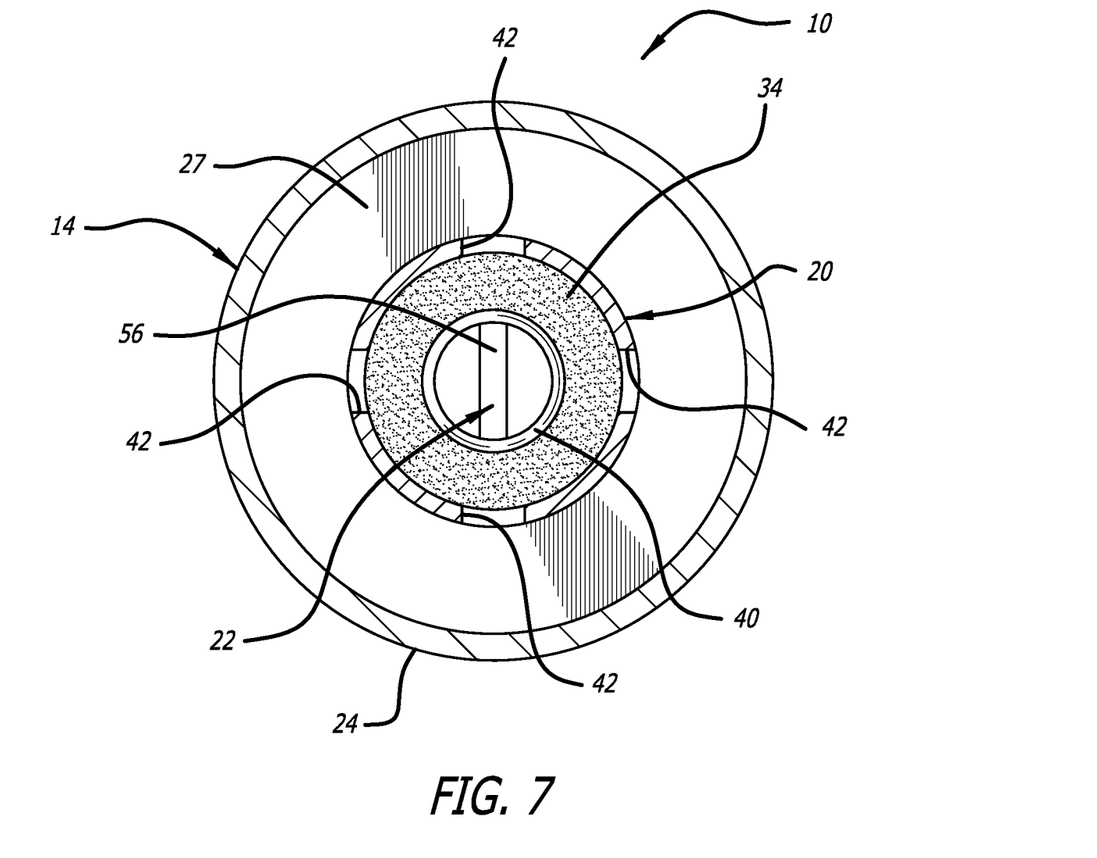
FIG. 7 is a cross-sectional view illustrative of the vaping atomizer embodiment of FIG. 1 taken along Line 7-7 of FIG. 4.

The heating-element housing 20 extends through at least a portion of the interior cavity 28. As depicted in FIGS. 1, 2, and 4, the heating-element housing 20 extends from a first end of the enclosure portion 14 adjacent the base portion 12 to a second end of the enclosure portion 14 adjacent the cap portion 16 and the inhaler portion 18. Given that the atomizer 10 is preferably used at or approximately at the orientation depicted in FIGS. 1 and 2, the first end is at the bottom of the interior cavity 28 and the second end is at the top of the interior cavity 28. The heating-element housing 20 includes threads 29A at one end thereof and threads 29B at the other end thereof. The threads 29A are received in a threaded opening 30 in the base portion 12 to attach the heating-element housing 20 to the base portion 12, and, as discussed below, the threads 29B are used in facilitating attachment of the cap portion 16 to the heating-element housing 20.

The cap portion 16 is attachable to the heating-element housing 20, and the cap portion 16 is seatable against (if not attachable) to the wall portion 24. Furthermore, the cap portion 16 and the inhaler portion 18 thereof are removable from the remainder of the atomizer 10 to provide access to the heating-element housing 20 and the interior cavity 28 within the enclosure portion 14.

As depicted in FIGS. 1-4, the cap portion 16 covers portions of the interior cavity 28 that are not occupied by the heating-element housing 20. Furthermore, the attachment between the cap portion 16 and the heating-element housing 20 can be liquid-tight, and the seating of the cap portion 16 against the wall portion 24 also can be liquid-tight. To that end, the inhaler portion 18 can include threads (not shown) for engaging the threads 29B on the heating-element housing 20, and the cap portion 16 can include a seal (not shown) for contacting the wall portion 24.

The interior cavity 28 can be filled with the supply of the vaping liquid, and the above-discussed liquid-tight attachment and seating of the cap portion 16 prevents the vaping liquid contained in the interior cavity 28 from leaking out while a user is using the atomizer 10. Furthermore, as discussed below, the heating-element housing 20 is configured to receive and vaporize the vaping liquid.

As depicted in FIG. 3, the heating-element housing 20 includes an interior cavity 31 extending between an open first end 32A and an open second end 32B. The open first end 32A is ultimately positioned adjacent the base portion 12, and the open second end 32B is ultimately positioned adjacent the inhaler portion 18.

The passages through base portion 12 can communicate with the open first end 32A, and the open second end 32B can communicate with an orifice 33 (FIGS. 3 and 5) formed through the inhaler portion 18. As such, air can be drawn through the openings 26 in the base portion 12, pass through the passages through the base portion 12, pass through the heating element 22, pass through the interior cavity 31 of the heating-element housing 20, pass through the orifice 33 of the of inhaler portion 18, and exit the atomizer 10.

The interior cavity 31 contains therein portions of the heating element 22 and a liquid-absorbing material 34. The heating element 22 electrically connects to the power source 11 so as to generate heat in the components thereof to facilitate vaporization of the vaping liquid contained in the liquid-absorbing material 34. Furthermore, the liquid-absorbing material 34 wraps around at least a portion of the surface of the heating-element housing forming the interior cavity 31.

As depicted in FIG. 3, the heating element 22 includes a contact portion 36, a plate portion 37, a cylindrical portion 38, an aperture 39 extending through the plate portion 37 and the cylindrical portion 38, and a coil portion 40. Besides being heated to facilitate vaporization of the vaping liquid contained in the liquid-absorbing material 34, the contact portion 36 transfers electrical energy from the power source 11 to the remainder of the heating element 22, the plate portion 37 is attached relative to the heating-element housing 20 adjacent the open second end 32B, the cylinder portion 38 and the coil portion 40 are received in the interior cavity 31, the cylinder portion 38 facilitates attachment of the coil portion 40 to the remainder of the heat element 22, and the coil portion 40 serves as a material holder for holding the liquid-absorbing material 34 against the surface of the interior cavity 31. Also, the relative attachment of the plate portion 37 to the heating-element housing 20 can be electrically isolating, and the aperture 39 affords passage of air drawn through the openings 26 into the heating-element housing 20.

Three or four apertures 42 are preferably provided in the heating-element housing 20 adjacent the attachment thereof to the base portion 12. The base portion 12 can include a recessed portion 44 in the upper surface 27 thereof adjacent the threaded opening 30 for receiving at least a portion of the heating-element housing 20 therein. The recessed portion 44 can afford placement of portions of the apertures 42 below the upper surface 27 of the base portion 12.

The apertures 42 are spaced around the heating-element housing 20, and the liquid-absorbing material 34 contained in the interior cavity 31 is exposed by the apertures 42. For example, the heating-element housing 20 can be at least partially cylindrical, and, when four of the apertures 42 are provided, the apertures 42 can be spaced 90° apart from one another, and, when four of the apertures 42 are provided, the apertures can be spaced 120° apart from one another. The apertures 42 are provided to allow the vaping liquid received in the interior cavity 28 of the enclosure portion 14 to pass into the interior cavity 31 of the heating-element housing 20. The liquid-absorbing material 34 is positioned in the interior cavity 31 during use of the atomizer 10. The vaping liquid stored in the interior cavity 28 seeps into the interior cavity 31 of the heating-element housing 20 via capillary action of the capillaries of the liquid-absorbing material 34 exposed by the apertures 42. The capillary action also allows the vaping liquid from the interior cavity 28 to wick into the remainder of the liquid-absorbing material 34. As such, the vaping liquid passes from the interior cavity 28 through the apertures 42 and saturates the liquid-absorbing material 34. Thereafter, heat from the heating element 22 vaporizes the vaping liquid absorbed by the liquid-absorbing material 34.

The liquid-absorbing material 34 can be made, for example, from a variety of materials including but not limited to natural and/or manmade fibrous materials including cotton, organic cotton, cellulose, hemp, silica, eco wool, polymeric fibers, stainless steel mesh, combinations thereof, and the like. Furthermore, the number of capillaries of the fibrous material can be varied via the material selected for liquid-absorbing material 34 and via the amount of compression applied to the selected materials. When filled with vaping liquid, the surface tension of the vaping liquid in the capillaries of the liquid-absorbing material 34 can create a hydraulic dam preventing the vaping material from the interior cavity 28 from flooding the interior cavity 31.

For the reasons discussed below, the apertures 42 are specially sized and shaped to accommodate a number of factors. Given that the atomizer 10 is preferably used at or approximately at the orientation depicted in FIGS. 1 and 2, the apertures 42 have their maximum side-to-side dimensions at or adjacent the bottoms thereof, and the apertures 42 have their minimum side-to-side dimension at or adjacent the tops thereof. Such dimensions correspond to the apertures 42 having areas greater in size adjacent the bottoms than adjacent the tops thereof.

For example, as depicted in FIGS. 1-4, 8A, 8B, and 8C, the apertures 42 can be shaped as triangles with first dimensions aligned with the mid-longitudinal axis in the bottom-to-top or top-to-bottom directions (e.g., dimensions A, C, and E in FIGS. 8A, 8B, and 8C), and have maximum side-to-side dimensions transverse to the first dimensions at or adjacent the bottoms of the apertures (e.g., dimensions B, D, and F in FIGS. 8A, 8B, and 8C), and have minimum side-to-side dimensions transverse to the first dimensions at or adjacent the tops of the apertures. More specifically, the apertures 42 can be generally shaped as triangles or triangles having rounded intersections between the sides thereof. Furthermore, the dimensions A, C, and E preferably can range from 3 to 10 mm, and the dimensions B, D, and F likewise preferably can range from 2 to 8 mm.

Another way of describing the shape of the apertures 42 in a preferred embodiment of the invention is being "candy corn" shaped or generally having the shape of the larger side profile of a piece of "candy corn." The apertures 42 can have other alternative shapes provided that they have maximum side-to-side dimensions at or adjacent the bottoms thereof, have minimum side-to-side dimensions at or adjacent the tops thereof, and correspondingly have areas greater in size adjacent the bottoms than adjacent the tops thereof. In a further preferred embodiment, the at least one aperture has a maximum dimension aligned with the mid-longitudinal axis, and a plane perpendicular to the mid-longitudinal axis extending through a midpoint of the maximum dimension aligned with the mid-longitudinal axis, where a first area of the at least one aperture above the plane being less than a second area of the at least one aperture below the plane.

Figure 8A:
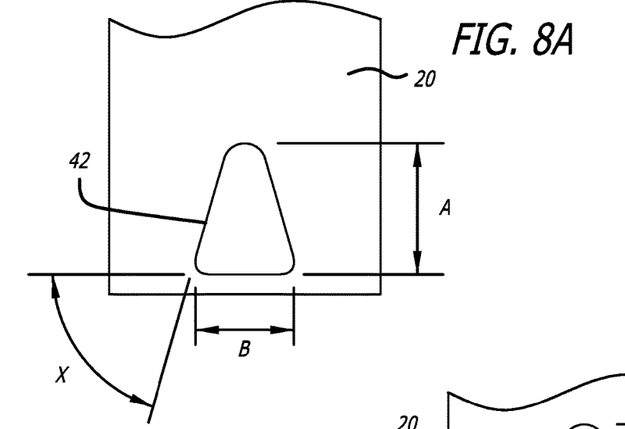
FIG. 8A is a partial elevational view illustrative of a first embodiment of an aperture(s) in a heating-element housing of the vaping atomizer embodiment of FIG. 1.
Figure 8B:
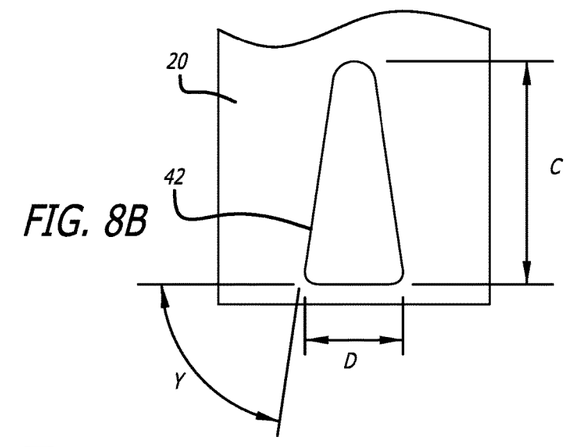
FIG. 8B is a partial elevational view illustrative of a second embodiment of an aperture(s) in the heating-element housing of the vaping atomizer embodiment of FIG. 1.
Figure 8C:
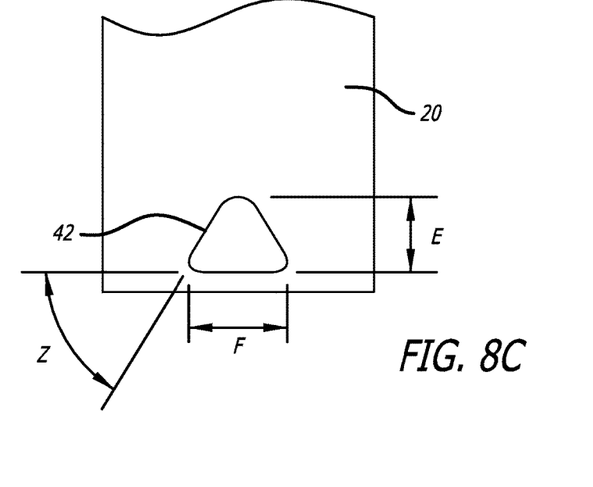
FIG. 8C is a partial elevational view illustrative of a third embodiment of an aperture(s) in the heating-element housing of the vaping atomizer embodiment of FIG. 1.

In a preferred embodiment of the present invention, the apertures 42 (FIGS. 8A, 8B, and 8C) are shaped generally as isosceles triangles although in a more preferred embodiment the intersections of the sides and base of the triangle are rounded or arcuate. Preferably, as depicted in FIGS. 8A and 8B, the sides of the isosceles triangles are equal in length to one another and the base is shorter in length than the sides. Alternatively, as depicted in FIG. 8C, the sides of the isosceles triangle are equal in length to one another and the base is longer in length than the sides. In one preferred embodiment, the intersection of the two sides with one another have a first arc of radius, and the intersection of each of the two sides with the base have a second arc of radius and a third arc of radius, respectively. The second and third arcs of radius are preferably equal to one another and in a further preferred embodiment the first, second, and third arcs of radius are equal to one another.

In another preferred embodiment of the present invention, the sides of the generally isosceles shaped triangles of the apertures 42 are at approximately 70 degree angles relative to the base of the triangle. In additional preferred embodiments these angles are approximately 60 degrees (see e.g., angle Z of FIG. 8C), 61 degrees, 62 degrees, 63 degrees, 64 degrees, 65 degrees, 66 degrees, 67 degrees, 68 degrees, 69 degrees, 71 degrees, 72 degrees, 73 degrees, 74 degrees, 75 degrees (see e.g., angle X of FIG. 8A), 76 degrees, 77 degrees, 78 degrees, 79 degrees, and 80 degrees (see e.g., angle Y of FIG. 8B).

In another preferred embodiment of the present invention, the sides of the generally isosceles shaped triangles of the apertures 42 are at approximately a 40 degree angle to one another. In additional preferred embodiments this angle is approximately 30 degrees, 31 degrees, 32 degrees, 33 degrees, 34 degrees, 35 degrees, 36 degrees, 37 degrees, 38 degrees, 39 degrees, 41 degrees, 42 degrees, 43 degrees, 44 degrees, 45 degrees, 46 degrees, 47 degrees, 48 degrees, 49 degrees, and 50 degrees.

In another preferred embodiment of the present invention, a maximum height of the generally isosceles shaped triangles of the apertures 42 is approximately 50 percent greater than a maximum width of the generally isosceles shaped. In additional preferred embodiments the maximum height can be one of approximately 40 or 41 or 42 or 43 or 44 or 45 or 46 or 47 or 48 or 49 or 51 or 52 or 53 or 54 or 55 or 56 or 57 or 58 or 59 or 60 percent greater than the maximum width.

While the apertures 42 have been described above as triangles, as isosceles triangles, generally shaped as triangles, as triangles having rounded intersections between the sides thereof, and as "candy corn shaped", the apertures 42 of a preferred embodiment also are shaped so as to permit a trapezoid to fit within the aperture 42 over a significant portion of the height of the aperture 42 such that the sides of the isosceles trapezoid align with and contact the sides of the aperture 42, and the larger bottom of the isosceles trapezoid is generally oriented toward the bottom of the aperture 42. In particular, in a preferred embodiment of the present invention, the trapezoids of the apertures 42 are more than 80 percent of the height of the apertures 42. In yet further preferred embodiments, the trapezoids of the apertures 42 are more than one of 75 or 70 or 65 or 60 or 55 or 50 percent of the height of the apertures 42. In a yet further preferred embodiment, the apertures 42 shaped so as to permit a trapezoid to fit within the aperture 42 as described above are more preferably isosceles trapezoids.

In each instance where a range of numbers have been provided with respect to the size and configuration of the apertures 42, such as, for degrees, height to width ratios, and percentages of height at least corresponding to the shape of the isosceles trapezoids the list of preferred ranges have been listed in this short hand fashion for convenience to the reader and should be interpreted the same as if a separate sentence were written for each number listed within the ranges as a separate preferred embodiment for each.

The apertures 42 are sized and shaped to both prevent the vaping liquid from flooding the interior cavity 31, and to accommodate uses of various vaping liquids having different viscosities.

Flooding is prevented by limiting the size of the apertures 42 to limit the area of the liquid-absorbing material 34 exposed through the apertures 42 in comparison to the maximum amount of the vaping liquid storable in the interior cavity 28. By limiting the sizes of the apertures 42, the maximum pressure on the liquid-absorbing material 34 through the apertures 42 can be limited to afford formation of an effective hydraulic dam by ensuring that the surface tension of the vaping liquid in the capillaries of the liquid-absorbing material 34 is not exceeded.

Furthermore, uses of various vaping liquids is accommodated by shaping the apertures 42 to accommodate passage of the vaping liquids having a range of viscosities. As discussed above, the apertures 42 are shaped to have areas greater in size adjacent the bottoms than adjacent the tops thereof, and sized to afford passage of vaping liquids having various viscosities. As such, vaping liquids having lower viscosities can pass through the entireties of the apertures 42, and vaping liquids having higher viscosities at least can pass through the bottom portions of the apertures 42. However, in both events, the liquid-absorbing material 34 can be saturated with the lower and higher viscosity liquids, respectively.

In view of these factors, it becomes clear that limiting the size of the apertures 42 must be balanced against the shapes and sizes necessary to accommodate a range of viscosities for the vaping liquids.

Additionally, the apertures 42 are shaped to inhibit dry hits from occurring due to the drying of portions of the liquid-absorbing material 34 during use of the atomizer 10. As discussed above, the interior cavity 28 of the enclosure portion 14 is filled with an amount of the vaping liquid. Typically, the interior cavity 28 is initially filled so that the level of the vaping liquid covers the entirety of each of the apertures 42 (and the areas of the liquid-absorbing material 34 exposed thereby) when the atomizer 10 is at or approximately at the orientation depicted in FIGS. 1 and 2.

During use of the atomizer 10, the level of the vaping liquid in the interior cavity 28 naturally decreases due to consumption thereof, and the level of the vaping liquid in the interior cavity 28 can drop below the level of the topmost portions of the apertures 42 and the areas of the liquid-absorbing material 34 exposed thereby. As such, areas of the liquid-absorbing material 34 exposed by the apertures 42 can no longer be covered by the vaping liquid due to such consumption. The shapes of the apertures 42 serve in preventing the liquid-absorbing material 34 from drying out in the areas of the liquid-absorbing material 34 uncovered by the vaping liquid and the areas of the liquid-absorbing material 34 in the interior cavity 31 above the levels of the vaping liquid in the interior cavity 28.

As discussed above, the shapes of the apertures 42 have areas greater in size adjacent the bottoms than adjacent the tops thereof. As such, the pressure of the vaping liquid contained in the interior cavity 28 on the liquid-absorbing material 34 exposed by the apertures 42 is greater in the areas of greater size. Because of these areas of greater size, the vaping liquid is forced into the liquid-absorbing material 34 even as the level of vaping liquid in the interior cavity 28 and the pressure applied by the vaping liquid on the liquid-absorbing material 34 exposed by the apertures 42 decreases. Via this pressure and the capillary action of the liquid-absorbing material 34, the upper portions of the liquid-absorbing material 34 (e.g., the areas of the liquid-absorbing material 34 uncovered by the vaping liquid and the areas of the liquid-absorbing material 34 in the interior cavity 31 above the levels of the vaping liquid in the interior cavity 28) are less likely to dry out because these portions are starved of the vaping liquid. By keeping substantially the entirety of the liquid-absorbing material wetted with the vaping liquid, the occurrence of dry hits during use of the atomizer 10 can be inhibited.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An atomizer for use with a vaping device, the atomizer comprising:
   a first end, an opposite second end, and a mid-longitudinal axis extending through the first and second ends;
   a base portion being provided at or adjacent the first end;
   an enclosure portion supported by the base portion and extending from the base portion toward the second end, the enclosure portion including an interior;
   a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion;
   a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture having a maximum dimension aligned with the mid-longitudinal axis, and a plane perpendicular to the mid-longitudinal axis extends through a midpoint of the maximum dimension aligned with the mid-longitudinal axis, a first area of the at least one aperture above the plane being less than a second area of the at least one aperture below the plane; and
   a heating element disposed in the second cavity of the heating-element housing, the heating element being at least partially surrounded by the liquid-absorbing material;
   wherein the first cavity is adapted to receive a vaping liquid so that the vaping liquid can pass from the first cavity to the second cavity through the at least one aperture, the liquid-absorbing material being configured to absorb the vaping liquid when passing through the at least one aperture; and
   wherein heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

2. The atomizer of claim 1, wherein the at least one aperture has a lower first area including the second dimension and an upper second area including the third dimension, the lower first area being greater than the upper second area.

3. The atomizer of claim 1, wherein the at least one aperture is generally shaped as a triangle.

4. The atomizer of claim 3, wherein the second dimension is located at a lower portion of the triangle, and the third dimension is located at an upper portion of the triangle.

5. The atomizer of claim 1, wherein the at least one aperture is at least partially recessed in the base portion.

6. The atomizer of claim 1, wherein the at least one aperture includes four apertures spaced apart from one another on the heating-element housing.

7. The atomizer of claim 6, wherein the heating-element housing is at least partially cylindrical, and the four apertures of the at least one aperture are spaced 90° apart from one another.

8. An atomizer for use with a vaping device, the atomizer comprising:
   a first end, an opposite second end, and a mid-longitudinal axis extending through the first and second ends;
   a base portion being provided at or adjacent the first end;
   an enclosure portion supported by the base portion and extending from the base portion toward the second end, the enclosure portion including an interior;
   a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion;
   a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture having a first maximum dimension aligned with the mid-longitudinal axis, a second maximum dimension perpendicular to the first maximum dimension, a first minimum dimension perpendicular to the first maximum dimension, and a plane perpendicular to the mid-longitudinal axis extends through a midpoint of the first maximum dimension aligned with the mid-longitudinal axis, a first area of the at least one aperture above the plane being less than a second area of the at least one aperture below the plane, the first minimum dimension being disposed in the first area, and the second maximum dimension being disposed in the second area;
   a heating element disposed in the second cavity of the heating-element housing, the heating element being at least partially surrounded by the liquid-absorbing material;
   wherein the first cavity is adapted to receive a vaping liquid so that the vaping liquid can pass from the first cavity to the second cavity through the at least one aperture, the liquid-absorbing material being configured to absorb the vaping liquid when passing through the at least one aperture; and
   wherein heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

9. The atomizer of claim 8, wherein the at least one aperture having a first dimension aligned with the mid-longitudinal axis, a maximum second dimension transverse to the first dimension, and a minimum third dimension transverse to the first dimension, the second dimension being disposed in the lower first area, and the third dimension being disposed in the upper second area, the second dimension being closer to the base portion than the third dimension.

10. The atomizer of claim 9, wherein the at least one aperture is generally shaped as a triangle.

11. The atomizer of claim 10, wherein the second dimension is located at a lower portion of the triangle, and the third dimension is located at an upper portion of the triangle.

12. The atomizer of claim 8, wherein the at least one aperture is at least partially recessed in the base portion.

13. The atomizer of claim 8, wherein the at least one aperture includes four apertures spaced apart from one another on the heating-element housing.

14. The atomizer of claim 13, wherein the heating-element housing is at least partially cylindrical, and the four apertures of the at least one aperture are spaced 90° apart from one another.

15. An atomizer for use with a vaping device, the atomizer comprising:
   a first end, an opposite second end, and a mid-longitudinal axis extending through the first and second ends;
   a base portion being provided at or adjacent the first end;
   an enclosure portion supported by the base portion and extending from the base portion toward the second end, the enclosure portion including an interior;
   a cap portion attachable and detachable from the enclosure portion and being provided at or adjacent the second end, the cap portion, when attached to the enclosure portion, covering at least a portion of the interior of the enclosure portion, and the cap portion, when detached from the enclosure portion, providing access to the interior, the cap portion including an inhaler portion including an opening extending through the cap portion;
   a heating-element housing extending through the interior of the enclosure from the base portion to the cap portion, a first cavity being at least partially formed between the enclosure portion and the heating-element housing, the heating-element housing forming a second cavity therein, the second cavity including a liquid-absorbing material disposed therein, and the second cavity communicating with the opening of the inhaler portion when the cap portion is attached relative to the enclosure portion, the heating-element housing including at least one aperture formed therein proximate the base portion, the at least one aperture being covered by the liquid-absorbing material inside the second cavity, the at least one aperture being generally shaped as a triangle, the at least one aperture having a maximum dimension aligned with the mid-longitudinal axis, and a plane perpendicular to the mid-longitudinal axis extends through a midpoint of the maximum dimension aligned with the mid-longitudinal axis, a first area of the at least one aperture above the plane being less than a second area of the at least one aperture below the plane; and a heating element disposed in the second cavity of the heating-element housing, the heating element being at least partially surrounded by the liquid-absorbing material;

wherein the first cavity is adapted to receive a vaping liquid so that the vaping liquid can pass from the first cavity to the second cavity through the at least one aperture, the liquid-absorbing material being configured to absorb the vaping liquid when passing through the at least one aperture; and wherein heat from the heating element is adapted to vaporize an amount of the vaping liquid when absorbed by the liquid-absorbing material, the second cavity being adapted to permit the vaporized vaping liquid to be removed from the second cavity through the opening of the inhaler portion.

16. The atomizer of claim 15, wherein the at least one aperture has a lower first area including the second dimension and an upper second area including the third dimension, the lower first area being greater than the upper second area.

17. The atomizer of claim 15, wherein the second dimension is located at a lower portion of the triangle, and the third dimension is located at an upper portion of the triangle.

18. The atomizer of claim 15, wherein the at least one aperture is at least partially recessed in the base portion.

19. The atomizer of claim 15, wherein the at least one aperture includes four apertures spaced apart from one another on the heating-element housing.

20. The atomizer of claim 6, wherein the heating-element housing is at least partially cylindrical, and the four apertures of the at least one aperture are spaced 90° apart from one another.

* * * * *